United States Patent [19]

Berg

[11] Patent Number: 5,580,427
[45] Date of Patent: Dec. 3, 1996

[54] SEPARATION OF BUTYRALDEHYDE FROM ETHANOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 554,764

[22] Filed: Nov. 7, 1995

[51] Int. Cl.$^6$ .............................. B01D 3/36; C07C 45/84
[52] U.S. Cl. .............................. 203/57; 203/60; 203/63; 203/65; 203/68; 568/492; 568/913
[58] Field of Search .................................. 203/60, 63, 68, 203/65, 57; 568/492, 496, 913

[56] References Cited

U.S. PATENT DOCUMENTS

| 4,383,893 | 5/1983 | Kaibel et al. | 568/913 |
| 4,523,041 | 6/1985 | Kawai et al. | 568/755 |
| 4,986,885 | 1/1991 | Driscoll et al. | 203/18 |

FOREIGN PATENT DOCUMENTS

| 0116534 | 5/1987 | Japan . | |
| 0196532 | 8/1988 | Japan . | |
| 0667134 | 2/1952 | United Kingdom | 203/68 |
| 0682487 | 11/1952 | United Kingdom | 203/63 |

*Primary Examiner*—Virginia Manoharan

[57] ABSTRACT

Butyraldehyde cannot be separated from ethanol by conventional distillation or rectification because they form a minimum boiling azeotrope. Butyraldehyde can be readily separated from ethanol by azeotropic distillation. Effective agents are ethyl formate, hexane and isopropyl ether.

1 Claim, No Drawings

SEPARATION OF BUTYRALDEHYDE FROM ETHANOL BY AZEOTROPIC DISTILLATION

FIELD OF THE INVENTION

This invention relates to a method of separating butyraldehyde from ethanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Butyraldehyde and ethanol form a minimum azeotrope boiling at 70.7° C. and containing 60.6% butyraldehyde and are thus impossible to separate by conventional distillation or rectification. Azeotropic distillation would be an attractive method of effecting the separation of butyraldehyde from ethanol if agents can be found that (1) will create a large apparent relative volatility between butyraldehyde and ethanol and (2) are easy to recover from these two compounds. Table 2 shows the relative volatility required to obtain 99% purity. With an agent giving a relative volatility of 1.4, only 38 actual plates are required.

TABLE 2

Theoretical and Actual Plates Required vs. Relative Volatility for Butyraldehyde - Ethanol Separation

| Relative Volatility | Theoretical Plates Required At Total Reflux, 99% Purity | Actual Plates Required 75% Efficiency |
|---|---|---|
| 1.2 | 52 | 70 |
| 1.3 | 35 | 47 |
| 1.4 | 28 | 38 |

OBJECTIVE OF THE INVENTION

The object of this invention is to provide a process or method of Azeotropic distillation that will enhance the relative volatility of butyraldehyde from ethanol in their separation in a rectification column. It is a further object of this invention to identify organic compounds which in addition to the above contraints, are stable, can be separated from butyraldehyde or ethanol and recycled to the azeotrope column with little decomposition

SUMMARY OF THE INVENTION

The objects of this invention are to provide a process for separating butyraldehyde from ethanol which entails the use of certain organic compounds as the agent in azeotropic distillation.

TABLE 3

Effective Azeotropic Distillation Agents For Separating Butyraldehyde From Ethanol

| Compounds | Relative Volatility |
|---|---|
| Ethyl formate | 1.3 |
| Hexane | 1.25 |
| Isopropyl ether | 1.4 |
| Ethyl ether | 1.2 |
| 2,2-Dimethoxypropane | 1.3 |

DETAILED DESCRIPTION OF THE INVENTION

I have discovered that certain organic compounds will greatly improve the relative volatility of butyraldehyde from ethanol and permit the separation of butyraldehyde from ethanol by rectification when employed as the agent in azeotropic distillation. Table 3 lists the compounds that I have found to be effective. They are ethyl formate, hexane, isopropyl ether, ethyl ether and 2,2-dimethoxypropane.

THE USEFULNESS OF THE INVENTION

The usefulness or utility of this invention can be demonstrated by referring to the data presented in Tables 1, 2 and 3. All of the successful agents show that butyraldehyde can be separated from ethanol by means of azeotropic distillation in a rectification column and that the ease of separation as measured by relative volatility is considerable.

WORKING EXAMPLES

1. Twenty grams of butyraldehyde, 40 grams of ethanol and 40 grams of ethyl formate were charged to a vapor-liquid equilibrium still and refluxed for five hours. Analysis indicated a vapor composition of 36.5% butyraldehyde, 63.5% ethanol; a liquid composition of 30.6% butyraldehyde, 69.4% ethanol. This is a relative volatility of 1.3.

2. Ten grams butyraldehyde, 50 grams of ethanol and 50 grams of isopropyl ether were charged to the vapor-liquid equilibrium still and refluxed for three hours. Analysis indicated a vapor composition of 19% butyraldehyde, 81% ethanol; a liquid composition of 14.4% butyraldehyde, 85.6% ethanol. This is a relative volatility of 1.4.

I claim:

1. A method for recovering butyraldehyde from a mixture consisting of butyraldehyde and ethanol which comprises distilling said mixture consisting of butyraldehyde and ethanol in the presence of an azeotrope forming agent, recovering butyraldehyde and the azeotrope forming agent as overhead product and obtaining the ethanol as bottoms product, wherein said azeotrope forming agent consists of one material selected from the group consisting of ethyl formate, hexane, isopropyl ether, ethyl ether and 2,2-dimethoxypropane.

* * * * *